United States Patent
Soma et al.

(10) Patent No.: US 8,071,758 B2
(45) Date of Patent: Dec. 6, 2011

(54) METHOD FOR PRODUCTION OF LIMULUS-POSITIVE GLYCOLIPID, THE LIMULUS-POSITIVE GLYCOLIPID, AND COMPOSITION CONTAINING THE LIMULUS-POSITIVE GLYCOLIPID

(75) Inventors: Gen-Ichiro Soma, Tokyo (JP); Chie Kohchi, Hiroshima (JP); Hiroyuki Inagawa, Shimonoseki (JP); Takashi Nishizawa, Tokushima (JP)

(73) Assignees: Gen-Ichiro Soma, Tokyo (JP); BioMedical Research Group Inc., Tokyo (JP); Macrophi, Inc., Takamatsu-shi (JP)

( * ) Notice: Subject to any disclaimer, the term of this patent is extended or adjusted under 35 U.S.C. 154(b) by 173 days.

(21) Appl. No.: 12/308,997

(22) PCT Filed: Feb. 28, 2007

(86) PCT No.: PCT/JP2007/053742
§ 371 (c)(1),
(2), (4) Date: Dec. 31, 2008

(87) PCT Pub. No.: WO2008/007476
PCT Pub. Date: Jan. 17, 2008

(65) Prior Publication Data
US 2010/0016577 A1    Jan. 21, 2010

(30) Foreign Application Priority Data
Jul. 14, 2006  (JP) .................................. 2006-194965

(51) Int. Cl.
C08B 37/00 (2006.01)
C07H 1/00 (2006.01)
C07H 15/00 (2006.01)

(52) U.S. Cl. ..................... 536/114; 536/123.1; 536/124; 536/4.1; 514/54; 514/25

(58) Field of Classification Search .................. 536/114, 536/123.1, 124, 4.1; 514/54, 25
See application file for complete search history.

(56) References Cited

U.S. PATENT DOCUMENTS 5,236,709 A * 8/1993 Soma et al. .............. 424/195.15
5,798,343 A    8/1998 Zahringer et al.

FOREIGN PATENT DOCUMENTS

JP  58-004724 A  1/1983
JP  06-263650 A  9/1994
JP  07-187949 A  7/1995
JP  07187949 A * 7/1995
JP  10-506612  6/1998

OTHER PUBLICATIONS

Shibayama et al.; JP 07187949 A, Jul. 25, 1995 (Machine English Translation).*
L. Ielpi et al., "Lipid-linked intermediates in the biosynthesis of xanthan gum," FEBS Ltters, vol. 130, No. 2, Aug. 3, 1981, p. 253-256 and a cover page.
Kensuke Miyake, "Innate immune recognition of lipopolysaccharide by Toll-like receptor 4/MD-2 and its manipulation by an antibody for therapeutic intervention in endotoxin shock," Japanese society for Immunology Sokai Gakujutsu Shukai Kiroku, vol. 34/Dai 34kai, Nov. 5, 2004, S1-1 (2 page).
Chie Kohchi et al., "Innate immunity regulatory action of fermented wheat extract," New Food Industry, vol. 48, No. 9, 2006, p. 19-27.
A.J. Ulmer et al., "Lipopolysaccharide: Structure, Bioactivity, Receptors, and Signal Transduction," Trends in Glycoscience and Glycotechnology, vol. 14, No. 76, Mar. 2002, p. 53-68.
C.O. Starnes, "Coley's toxins in perspective," Nature, vol. 357, May 7, 1992, p. 11-12.
T. Nishizawa et al., "Homeostasis as regulated by activated macrophage. I. Lipopolysaccharide (LPS) from wheat flour: isolation, purification and some biological activities," Chem.Pharm.Bull., vol. 40, No. 2, 1992, p. 479-483.
Hiroyuki Inagawa et al., "Therapeutic and Protective Effects of a Water Extract of Wheat Flour Having Limulus-Positive Substance (LPSw) Against Several Kinds of Diseases," Biotherapy, Apr. 1991, vol. 5, No. 4, p. 617-621.
Kiyoshi Takeda et al., "Toll-like receptors in innate immunity," International Immunology, vol. 17, No. 1, 2005, p. 1-14.
Seikagaku Jiten 2nd edition, Tokyo Kagaku Dojin (1990), p. 1419.
International Search Report dated Jun. 5, 2007, issued on PCT/JP2007/053742.
Written Opinion of the International Searching Authority issued on PCT/JP2007/053742.

* cited by examiner

*Primary Examiner* — Shaojia Anna Jiang
*Assistant Examiner* — Michael C Henry
(74) *Attorney, Agent, or Firm* — Edwards Wildman Palmer LLP

(57) ABSTRACT

It has been found that a *limulus*-positive glycolipid is present in xanthan gum derived from *Xanthomonas*, which has been commercially available and eaten for many years, and this was purified, and it has been found that this *limulus*-positive glycolipid has an immunopotentiation effect. A method for safely and inexpensively producing the *limulus*-positive glycolipid containing an immunopotentiator at high concentrations is provided. The method for producing the *limulus*-positive glycolipid of the present invention comprises extracting the *limulus*-positive glycolipid from xanthan gum. A *limulus*-positive glycolipid composition containing the *limulus*-positive glycolipid can be used for various applications such as pharmaceuticals, pharmaceuticals for animals, quasi drugs, cosmetics, foods, functional foods, feedstuff and bath agents.

2 Claims, No Drawings

METHOD FOR PRODUCTION OF LIMULUS-POSITIVE GLYCOLIPID, THE LIMULUS-POSITIVE GLYCOLIPID, AND COMPOSITION CONTAINING THE LIMULUS-POSITIVE GLYCOLIPID

TECHNICAL FIELD

The present invention relates to a method for producing a xanthan gum *limulus*-positive glycolipid which is an immunopotentiator and is safe when added in pharmaceuticals, quasi drugs, cosmetics, functional foods, feedstuff, fertilizers and bath agents for plants and animals such as mammals including humans (specifically domestic animals, pet animals, etc.), birds (specifically farmed chicken, pet birds, etc.), amphibian animals, reptiles, fish (specifically pet fish, etc.) and invertebrates, and a composition containing a *limulus*-positive glycolipid.

BACKGROUND ART

It is an urgent problem to establish disease prevention and therapeutic methods including infection prevention technology for mammals including humans (specifically domestic animals, pet animals, etc.), birds (specifically farmed chicken, pet birds, etc.), amphibian animals, reptiles, fish (specifically pet fish, etc.) and invertebrates. Furthermore, in order to achieve this, the methods using no chemicals, without environmental pollution, without producing resistant bacteria and without accumulation in the human body are strongly required. The present inventors have already found for the above problems that the immunopotentiators derived from natural products safely achieve disease prevention and therapeutic effects (Non-patent Document 1). As one example thereof, it is possible to use lipopolysaccharide obtained from *Pantoea agglomerans* which is a resident microbiota with wheat flour (Non-patent Document 1). It has been known that a *limulus*-positive glycolipid has a potent immunoenhancing activity (Non-patent Document 2). This *limulus*-positive glycolipid includes so-called lipopolysaccharide. It has been known that lipopolysaccharide is a major component of an outer wall of a cell of gram-negative bacteria as well as a major component of Coley's vaccine and has a potent immunopotentiation activity (Non-patent Document 3).

The present inventors have found that a *limulus*-positive glycolipid is present in wheat flour, a part thereof is lipopolysaccharide of a resident microbiota with wheat and they strongly potentiate innate immunity (Non-patent Document 4). And, the above two potentiate innate immunity safely and potently and exhibit protective and therapeutic effects on various diseases including infectious diseases by administering them percutaneously or orally (Non-patent Document 5). Furthermore, the present inventors have reported that a fermented wheat extract which is a novel immunopotentiator, not only in which the content of lipopolysaccharide derived from *Pantoea agglomerans* is increased, but also which contains the component derived from wheat by fermenting wheat flour with *Pantoea agglomerans* which is a resident microbiota with wheat flour, exerts an effect for infection prevention as a safe and trouble-free natural material in place of antibiotic substances or chemicals in the fields of animal industry and aquaculture.

A basic structure of lipopolysaccharide is composed of lipid referred to as lipid A and various types of sugars (polysaccharide) covalently bound thereto. A portion subsequent to lipid A is composed of R core which has a relatively uniform structure in related species and a subsequent O-antigen polysaccharide portion which has a different structure depending on the species (Non-patent Document 7). The O-antigen has a repeating structure of the same oligosaccharide characteristic for LPS (lipopolysaccharide) (Non-patent Document 1). Therefore, lipopolysaccharide generally forms a mixture having multiple molecular weights. It has also been known that lipopolysaccharide has a different structure depending on the microorganism which it is derived from. For example, lipopolysaccharide derived from *Salmonella* and lipopolysaccharide derived from *Escherichia coli* are different in structure and also in biological activity. However, in general, it is not easy to determine the structure of lipopolysaccharide. Thus, details of the structure and function of lipopolysaccharide in many gram negative bacteria have not been known. Thus, it has been described that lipopolysaccharide has a novel structure based on its functional difference.

Moreover, it has been demonstrated in recent studies that lipopolysaccharide activates innate immunity via TLR4 (Non-patent Document 6). It has been found that the lipid A moiety of lipopolysaccharide is essential for binding to TLR4 and a polysaccharide moiety greatly affects efficiency of intracellular signal transduction of TLR4. From the above, it is speculated that the difference in cellular response to lipopolysaccharide is attributed to a structural difference.

It is important in establishing the usefulness of lipopolysaccharide to confirm that percutaneously or orally administered lipopolysaccharide is safe and trouble-free. Thus, the gram negative bacteria used for producing and fermenting foods since ancient times have gained focus. That is, if *limulus*-positive glycolipid, inter alia lipopolysaccharide is present in the gram negative bacteria used for producing foods or provided for human consumption with fermented products, this fact confirms eating experience for *limulus*-positive glycolipid or lipopolysaccharide. This is a finding which strongly shows that percutaneously or orally administered lipopolysaccharide is safe and trouble-free, as well as encouraging the development of new health care products such as cosmetics and foods, and pharmaceuticals using these substances.

[Non-patent Document 1] Chie Kohchi et al., "Innate Immunity Regulatory Action of Fermented Wheat Extract," New Food Industry (2006) Vol. 48, p. 19-27.

[Non-patent Document 2] Ulmer, A. J. et al., "Lipopolysaccharide: Structure, Bioactivity, Receptors, and Signal Transduction," Trends in Glycoscience and Glycotechnology, (2000) Vol. 14, p. 53-68.

[Non-patent Document 3] Starnes, C. O., "Coley's Toxins in Perspective.," Nature, (1992) Vol. 357, p. 11-12.

[Non-patent Document 4] Nishizawa, T. et al., Chem. Pharm. Bull., (1992) Vol. 40, p. 479-483.

[Non-patent Document 5] Hiroyuki Inagawa et al., "Therapeutic and Preventive Effect of Lipopolysaccharide (LPSW) having Macrophage Activation Action and Derived from Wheat of Various Diseases.," Biotherapy, (1991) Vol. 5, p. 617-621.

[Non-Patent Document 6] Kiyoshi Takeda et al., "Toll-like Receptors in Innate Immunity.," International Immunology, Vol. 17, p. 1-14.

[Non-patent Document 7] Seikagaku Jiten 2nd Edition (1990), Tokyo Kagaku Dojin, p. 1949.

DISCLOSURE OF THE INVENTION

Problem to be Solved by the Invention

In order to orally or percutaneously administer to humans or animals, safety supported with eating experience is required. For example, acetic acid bacterium used for making a vinegar is gram negative bacterium, its microbial cell component is included in its fermented product, and thus can be said to have been eaten for many years. *Pantoea agglomerans* supplies folic acid required for lactic acid growth of rye breads, and a considerable amount of its microbial cell component is ingested when rye bread is eaten.

Xanthan gum is polysaccharide produced from *Xanthomonas campestris* which is gram negative bacterium, and is composed of mannose, glucose and glucuronic acid. In xanthan gum, β-1,4-linked glucose is a main chain, and in a side chain, two molecules of mannose and glucuronic acid are bound for every other glucose residue in the main chain. Xanthan gum has high viscosity, is stable in relation to acids, salts and heat, and is widely used as a thickener for foods. It was introduced in Japan about 30 years ago, and currently 1,300 tons or more of xanthan gum is annually consumed. From these, xanthan gum is a product fermented with gram negative bacterium, having been eaten for many years.

In this application, it has been found that *limulus*-positive glycolipid which had not been known until now is present in xanthan gum derived from *Xanthomonas*, which has been commercially available and eaten for many years, and this was purified, and it has been found that this *limulus*-positive glycolipid has an immunopotentiation effect.

Means for Solving the Problems

The method for producing the *limulus*-positive glycolipid of the present invention comprises extracting the *limulus*-positive glycolipid from xanthan gum.

The *limulus*-positive glycolipid of the present invention is obtained by the above method for producing the *limulus*-positive glycolipid.

The *limulus*-positive glycolipid composition of the present invention contains the above *limulus*-positive glycolipid.

The *limulus*-positive glycolipid composition is a pharmaceutical, a pharmaceutical for animals, a quasi drug, a cosmetic, a food, a functional food, a feedstuff or a bath agent.

Effect of the Invention

According to the present invention, it is possible to obtain trouble-free and safe *limulus*-positive glycolipid because it has been found that *limulus*-positive glycolipid is present in xanthan gum which has been commercially available and eaten for many years. This *limulus*-positive glycolipid can be used for various applications such as health care products and pharmaceuticals containing this because the *limulus*-positive glycolipid has been purified and it has been found that this has an immunopotentiation effect.

The present specification incorporates contents disclosed in the specification and drawings in Japanese Patent Application No. 2006-194965 which is a basis of priority of this application.

BEST MODES FOR CARRYING OUT THE INVENTION

Extraction of *Limulus*-Positive Glycolipid from Xanthan Gum

Examples

1) Extraction of *Limulus*-Positive Glycolipid from Xanthan Gum

Xanthan gum (1.00 g) (Dainippon Sumitomo Pharma Co., Ltd.) was added to one liter of phosphate buffered saline (PBS), and homogenized using a polytron at a scale of 6 for 10 minutes. A polymyxin B immobilized resin (5 ml) (Affiprep polymyxin support supplied from BIO-RAD, California) was added to the resulting PBS solution of 0.1% (w/v %) xanthan gum, and the solution was stirred using a magnetic stirrer for 4 hours. It has been known that polymyxin B is bound to a molecule such as lipid A having a high lipid-solubility. After stirring, the solution was transferred to a 50 ml centrifuge tube, which was then centrifuged at 2,000 rpm at room temperature for 10 minutes. After completing the centrifugation, the supernatant was discarded, and Affiprep polymyxin support was collected as a precipitate. 10 ml of PBS was added to the precipitate, stirred, and a precipitate was collected by the centrifugation at 2,000 rpm at room temperature. 5 ml of an aqueous solution of 0.02N sodium hydroxide was added to the precipitate, stirred for one minute, and centrifuged at 2,000 rpm at room temperature for 10 minutes. After completing the centrifugation, the supernatant was collected in another container. 5 ml of an aqueous solution of 0.02N sodium hydroxide was added again to a precipitate, stirred for one minute, and centrifuged at 2,000 rpm at room temperature for 10 minutes. After completing the centrifugation, two supernatants were combined. Immediately, 1 ml of 1 mol/liter (M) tris hydrochloride, pH 7.0 was added to neutralize the supernatants. It was identified by a phenol-sulfuric acid method that the resulting solution contained a sugar. Thus, this solution was made a *limulus*-positive glycolipid-containing extracted solution from xanthan gum.

The *limulus*-positive glycolipid was measured using Endospecy (supplied from Seikagaku Corporation; *limulus* test which does not react with β-1,3-glucan), and about 4 mg of the *limulus*-positive glycolipid was present. Because about 5 mg of the *limulus*-positive glycolipid was contained in xanthan gum, about 80% was yielded.

2) Measurement of Immunopotentiation Effect of *Limulus*-Positive Glycolipid

The *limulus*-positive glycolipid was added to RAW264.7 which was a cultured murine macrophage lineage cell line, and the production of nitrogen monoxide from the cells was measured.

Because RAW264.7 cells were weakly adherent cells, the cells were collected by pipetting from a culture flask and the cell concentration was adjusted to $8 \times 10^5$ cells/ml using a medium. A cell suspension (100 μl) was transferred to each well of a 96-well flat bottomed plate, which was used for a test after 6 hours when the cells were almost adhered.

A concentration of the *limulus*-positive glycolipid was adjusted equivalent to 4000 ng/ml of a lipopolysaccharide-concentration in *Pantoea agglomerans*. A serial dilution for 5 scales by 10 times was further performed. Each diluted solution was further diluted twice with the medium, and each diluted solution was further diluted twice with the medium containing 40 μg/ml polymyxin B. The resulting solution was used as a preparation for adding to the well in which the cells had been added.

Simultaneously, lipopolysaccharide (LPSx) purified from *Xanthomonas campestris* was also examined. 100 μl of each preparation was added to each well to which the cells had been previously added in the 96-well flat bottomed plate. The cells were cultured in a 5% carbon dioxide gas incubator at 37° C. for 20 hours. After completing the culture, 50 μl of the culture supernatant was collected. The amount of nitrous acid which was a metabolite of nitrogen monoxide in the medium was measured using Griess reagent according to standard methods.

Measurement results were shown in Tables 1 and 2. The *limulus*-positive glycolipid extraction solution from xanthan gum at concentrations of 100 ng/ml or higher exhibited production of NO from RAW264.7 cells. An NO production ability of LPSx was 22 times higher than that of the *limulus*-positive glycolipid when compared at 7.0 µM (the amount of the *limulus*-positive glycolipid required to be added for obtaining 7.0 µM of a nitrous acid concentration was 2.8 ng/ml whereas the amount of LPSx was 61.2 ng/ml, 61.2/2.8=22). In polymyxin B-adding groups, the NO production was not observed by both samples at 100 ng/ml, but was observed at 1,000 ng/ml. Thus, it was identified that they had a structure bound to polymyxin B.

TABLE 1

Ability of limulus-positive glycolipid from xanthan gum to induce NO production from RAW264.7 cells

| Added concentration (ng/ml) | Nitrous acid concentration(µM) | |
|---|---|---|
| | LPSx | Limulus-positive glycolipid from xanthan gum |
| 0 | 1.61 ± 0.22 | 1.54 ± 0.22 |
| 0.1 | 1.69 ± 0.24 | 1.39 ± 0.34 |
| 1 | 3.84 ± 0.52 | 1.98 ± 0.49 |
| 10 | 10.65 ± 0.65 | 2.28 ± 0.29 |
| 100 | 12.36 ± 0.50 | 8.28 ± 0.11 |
| 1000 | 14.13 ± 0.42 | 13.69 ± 0.27 |

Each measurement value was shown by mean±standard deviation of 4 examples.

TABLE 2

Ability of limulus-positive glycolipid from xanthan gum pretreated with polymyxin B to induce NO production from RAW264.7 cells.

| Added concentration (ng/ml) | Nitrous acid concentration(µM) | |
|---|---|---|
| | LPSx | Limulus-positive glycolipid from xanthan gum |
| 0 | 1.91 ± 0.36 | 1.98 ± 0.34 |
| 0.1 | 2.28 ± 0.29 | 2.21 ± 0.21 |
| 1 | 2.06 ± 0.26 | 1.76 ± 0.27 |
| 10 | 1.84 ± 0.22 | 1.76 ± 0.33 |
| 100 | 3.47 ± 0.25 | 2.43 ± 0.15 |
| 1000 | 5.84 ± 0.45 | 9.17 ± 0.50 |

Each measurement value was shown by mean±standard deviation of 4 examples.

From the above results, it has been found that the *limulus*-positive glycolipid from xanthan gum has action to induce the NO production from macrophages, but is different from lipopolysaccharide (LPSx) obtained from *Xanthomonas* microbial cells in biological activity. These results show that the structural difference is present between them.

3) Measurement of Molecular Weight of *limulus*-Positive Glycolipid Extracted from Xanthan Gum A molecular weight of the *limulus*-positive glycolipid extracted from xanthan gum was examined. Thus, 4 µg of *limulus*-positive glycolipid was mixed with a sample buffer, and sodium dodecyl sulfate polyacrylamide gel electrophoresis (SDS-PAGE) using tricine was performed. After electrophoresis, silver staining by Sil-Best Stainkit (Cat. No. 30642-41, Nacalai Tesque, Japan) was performed for the purpose of visualizing the molecule of lipopolysaccharide. Prestained Protein Marker, Broad Range (Premixed Format) (Cat. No. 7708L, NEW ENGLAND Biolabs) was used as a molecular weight size marker. As a result, the LPSx sample showed many ladder-like bands in 2,000 to 4,500 Daltons (Da) and 30 to 80 kDa. In the *limulus*-positive glycolipid extracted from xanthan gum, the bands were detected in 2,000 to 4,000 Da.

The molecular weights of the *limulus*-positive glycolipid extracted from xanthan gum are 2,000 to 4,000 Da whereas the molecular weights of LPSx were 2,000 to 4,500 Da and 30 to 80 kDa. This result shows that a structural difference is present between them.

4) Antigenic Difference Between *limulus*-Positive Glycolipid Extracted from Xanthan Gum and LPSx If there is a structural difference between the *limulus*-positive glycolipid extracted from xanthan gum and lipopolysaccharide (LPSx) obtained from *Xanthomonas* microbial cells, the difference of antigens occurs and the reactivity of antibodies is likely different. Thus, the *limulus*-positive glycolipid extracted from xanthan gum was stained with a monoclonal antibody against LPSx. The *limulus*-positive glycolipid was dropped on a polyvinylidene fluoride (PVDF) membrane (supplied from BIO-RAD), and subsequently non-specific reactions were blocked by incubating the PVDF membrane in PBS containing 3% bovine serum albumin (BSA) at room temperature for 30 minutes (blocking). Subsequently, the PVDF membrane was washed five times with Tris buffered saline (TBS: 20 mM Tris HCl, pH 7.5, 150 mM NaCl) containing 0.05% Tween 20. After washing, 5 ml of the medium containing an antibody specific to lipopolysaccharide obtained from the *Xanthomonas* microbial cell as a primary antibody was added and reacted at room temperature for 60 minutes.

(the monoclonal antibody specific for *Xanthomonas* lipopolysaccharide was made as follows. Heated and killed *Xanthomonas* bacteria were mixed with complete Freund's adjuvant, and 1×10$^8$ bacteria per mouse were administered intraperitoneally to BALB/c mice. The intraperitoneal administration was repeated three times at intervals of two weeks. Three days after the final administration, cells were collected from the spleen, and fused with myeloma cells (P3U1) using 50% polyethylene glycol (average molecular weight: 1000). The fused cells were suspended in HAT medium containing 10% FBS (fetal bovine serum), and cultured in a 96-well flat bottomed plate at 37° C. under 5% $CO_2$ and left stand for 7 days. Culture supernatants from the wells where colonies had formed were assayed by ELISA (Enzyme-Linked Immunosorbent Assay) publicly known and commonly used using *Xanthomonas* lipopolysaccharide as the antigen. The cells producing the monoclonal antibody obtained above were cloned by a limiting dilution method publicly known and commonly used. As a result, 21 murine monoclonal IgG antibodies against *Xanthomonas* lipopolysaccharide were obtained.)

Subsequently, the PVDF membrane was washed five times with Tris buffered saline (TBS: 20 mM Tris HCl, pH 7.5, 150 mM NaCl) containing 0.05% Tween 20. After washing, 5 ml of alkaline phosphatase-conjugated anti-murine IgM goat immunoglobulin (A9688, Sigma) diluted 1000 times with PBS containing 1% BSA was added as a secondary antibody, and the membrane was reacted at room temperature for 60 minutes. Subsequently, the membrane was washed five times with TBS containing 0.05% Tween 20. After washing, 5 ml of alkali phosphatase buffer (50 mM Tris HCl, pH 9.5, 1 mM $MgCl_2$) containing a chromogenic substrate, 0.0165% 5-bromo-4-chloro-3 indolyl phosphate (025-08651, Wako Pure Chemical Industries Ltd., Japan) and 0.033% nitroblue tetrazolium (N-6876, Sigma) was added, and thereafter the PDVF membrane was transferred into distilled water to stop the reaction. As a result, LPSx was detected by all of the 21 antibodies, but the *limulus*-positive glycolipid from xanthan gum did not react with the 20 antibodies, and reacted with only one antibody. In this way, it was found that the *limulus*-positive glycolipid extracted from xanthan gum has antigenicity which is different from that of lipopolysaccharide (LPSx) from *Xanthomonas*. From this result, it has been shown that the structure of the *limulus*-positive glycolipid extracted from xanthan gum is different from the structure of lipopolysaccharide (LPSx) from *Xanthomonas*.

5) Example of Functional Food of *limulus*-Positive Glycolipid Extracted from Xanthan Gum
Production of Candy Containing *limulus*-Positive Glycolipid Extracted from Xanthan Gum The mixture as raw materials obtained by adding the *limulus*-positive glycolipid extracted from xanthan gum produced in 1) to granulated sugar, starch syrup and water at a ratio of 5:5:5:1 was heated and boiled down at 120 to 140° C., then cooled on a steel plate for cooling, stretched into a bar-shape and molded into a small round shape of around 1 g to produce a candy containing the *limulus*-positive glycolipid extracted from xanthan gum.

An appropriate amount of this candy was added to 20 ml of water and dissolved by heating. A mass of the *limulus*-positive glycolipid extracted from xanthan gum in this solution was measured, and the amount was 6 μg/g. This candy was ingested by 6 males and females who had colds with a sore throat. Immediately after, a questionnaire regarding the sore throat was conducted. All six persons felt that their respective throats had abated (one-sample sign test: $p<0.03$).

All publications, patents and patent applications cited herein are directly incorporated herein by reference.

The invention claimed is:

1. A method for producing a limulus-positive glycolipid comprising extracting the limulus-positive glycolipid, having a molecular weight of about 2000 to about 4000 Da measured by SDS-PAGE, from xanthan gum,
    the extracting process comprising a step of adding a polymyxin B immobilized resin to a buffer solution containing the xanthan gum.

2. The method for producing a limulus-positive glycolipid according to claim 1 wherein a presence of the limulus-positive glycopilid in the extractant is measured by a limulus test.

* * * * *